United States Patent [19]

Anderson

[11] 4,115,200
[45] Sep. 19, 1978

[54] INOCULATOR

[75] Inventor: Joseph A. Anderson, Denver, Colo.

[73] Assignee: Benny F. Mertens, Denver, Colo.; a part interest

[21] Appl. No.: 712,685

[22] Filed: Aug. 9, 1976

[51] Int. Cl.$^2$ .............................................. C12K 1/04
[52] U.S. Cl. .................................. 195/127; 23/230 B; 422/63; 141/237; 141/238; 195/120
[58] Field of Search .................. 195/120, 127, 139; 141/237, 238; 23/230 B, 253, 259

[56] References Cited

U.S. PATENT DOCUMENTS

| | | | |
|---|---|---|---|
| 3,536,449 | 10/1970 | Astle | 141/237 X |
| 3,728,227 | 4/1973 | Elson et al. | 195/127 |
| 3,742,187 | 6/1973 | Folus | 195/120 X |
| 3,775,256 | 11/1973 | Risinger | 195/127 X |
| 3,912,596 | 10/1975 | Haque et al. | 195/127 |

OTHER PUBLICATIONS

Ann Baillie and R. J. Gilbert, Automation, Mechanization and Data Handling in Microbiology; Academic Press; pp. 175-188; 1970.

Primary Examiner—Alvin E. Tanenholtz
Assistant Examiner—Robert J. Warden
Attorney, Agent, or Firm—Sheridan, Ross, Fields & McIntosh

[57] ABSTRACT

A motor driven inoculator is provided wherein a plurality of bacteriological transfer loops are mounted on a common head and are activated in response to the positioning of a tray of inoculum to cause the head to be lowered and then raised so that the loops pick up a sample of inoculum. The subsequent positioning of an antibiotic or antimicrobic microtube plate, etc. causes the head to be lowered and raised a second time so that the loops are lowered into the plate to place samples of inoculum in each of a plurality of wells in the plate by dispersion. The removal of the antibiotic plate initiates a sterilizing cycle wherein the head is lowered and raised a third time whereby the loops are heated to a very high temperature by passing electrical current therethrough to volatilize all material thereon and then they are subsequently air cooled prior to the beginning of the next cycle. In an alternative embodiment the inoculum on the loops may be dispersed by percussion.

The inoculum tray includes a plurality of grooves and ridges so that a minimal amount of inoculum is necessary for use in placing samples on the loops by dipping.

9 Claims, 31 Drawing Figures

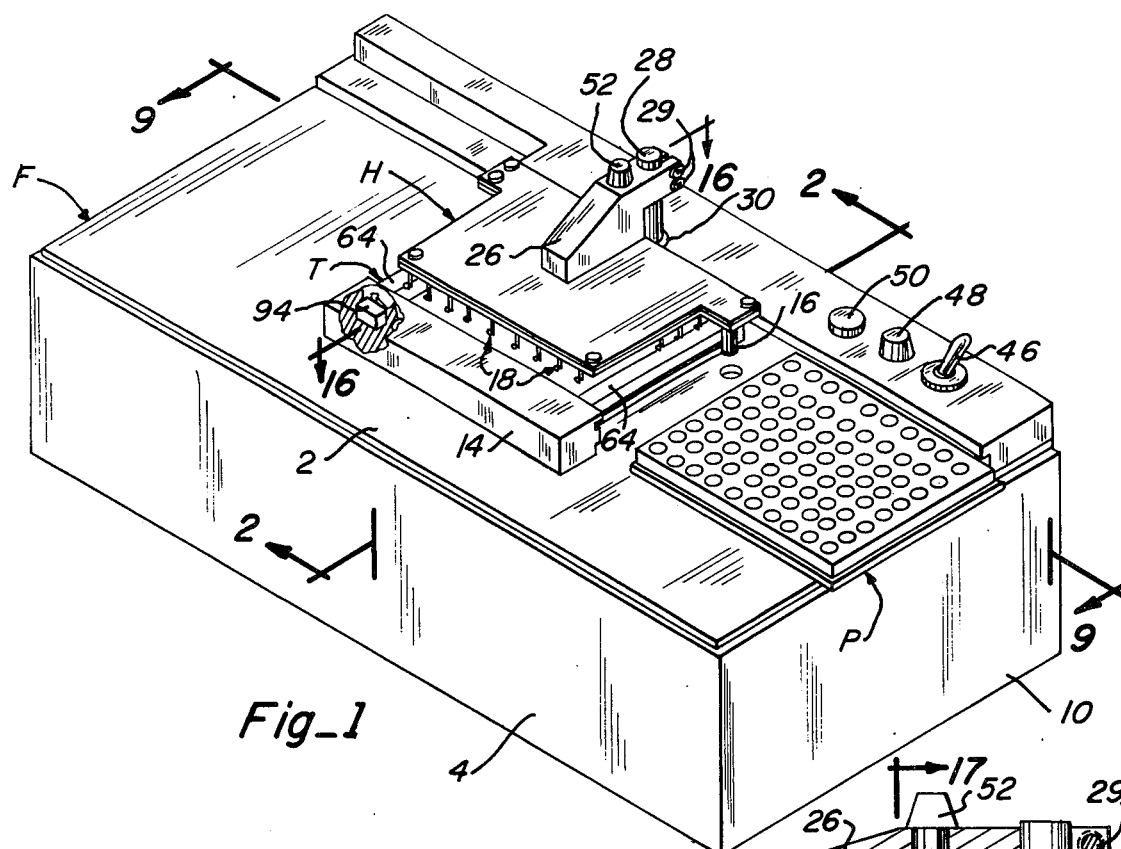
Fig_1
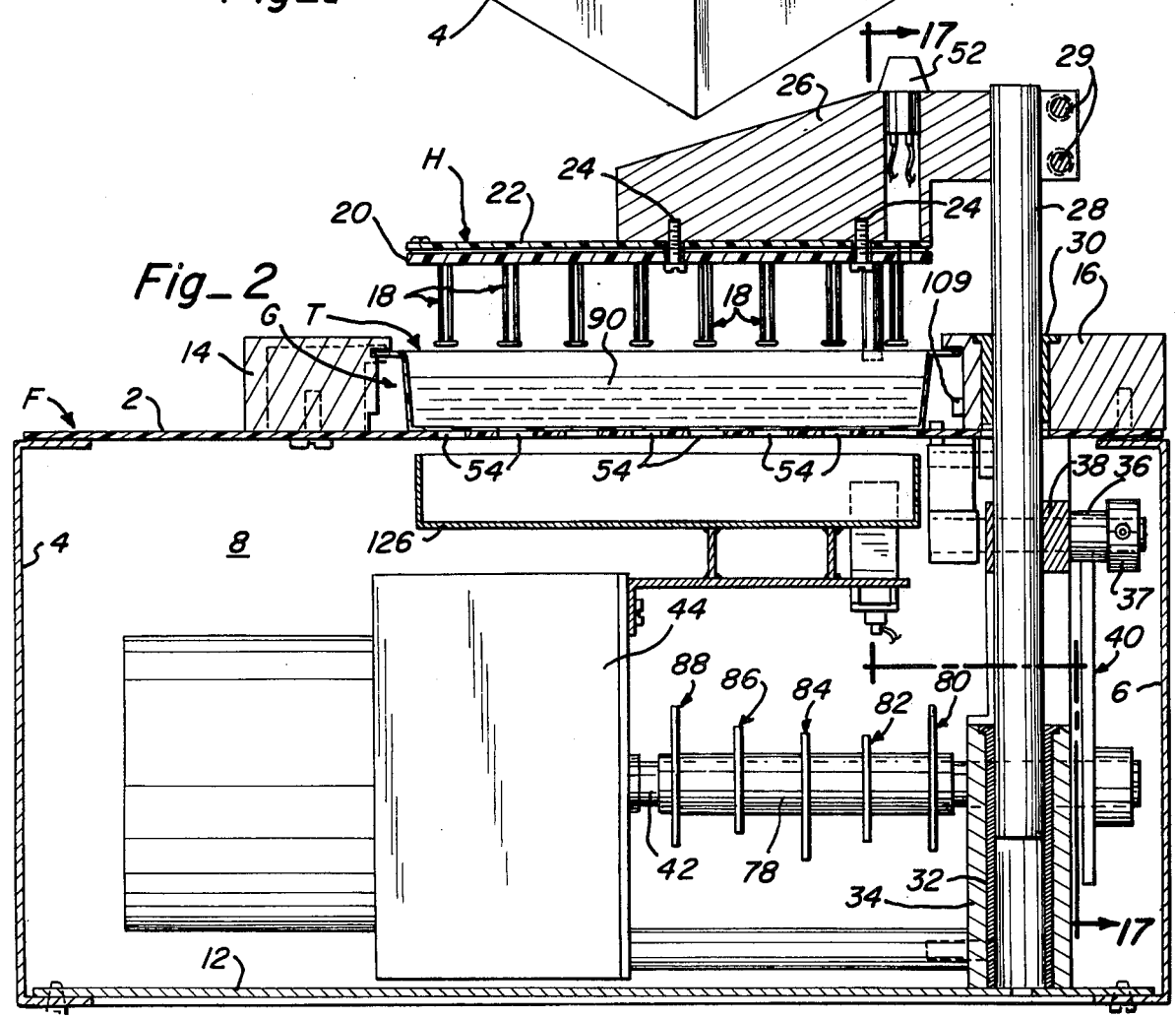
Fig_2

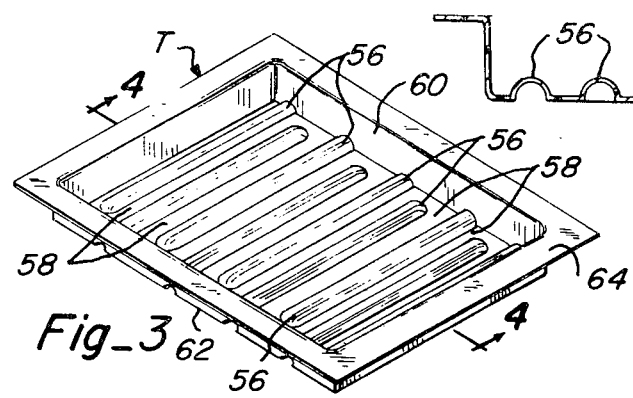
Fig_3  Fig_4
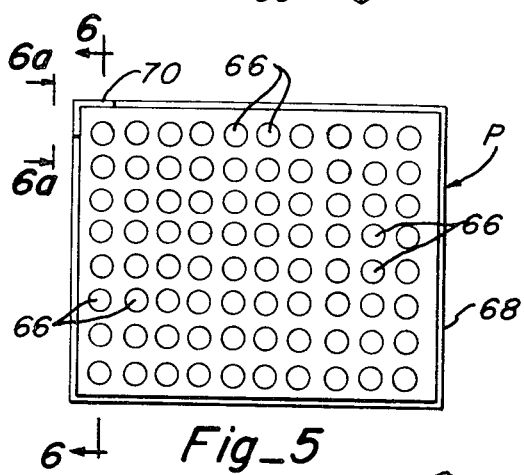
Fig_5
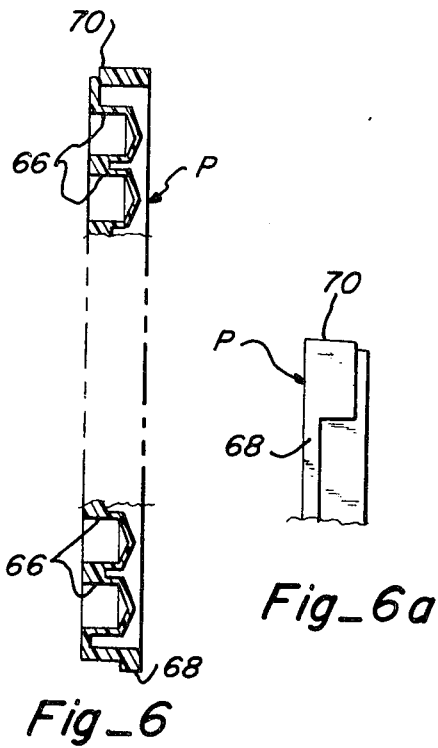
Fig_6  Fig_6a
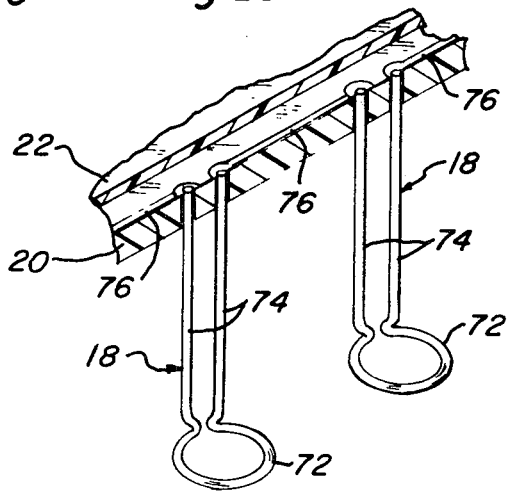
Fig_7
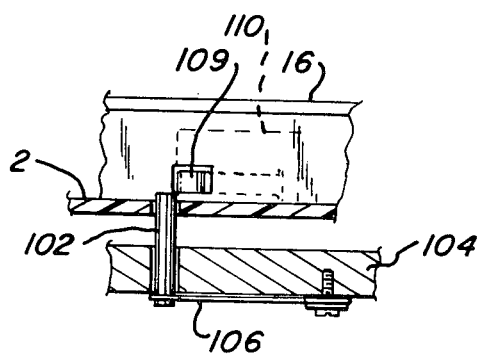
Fig_8

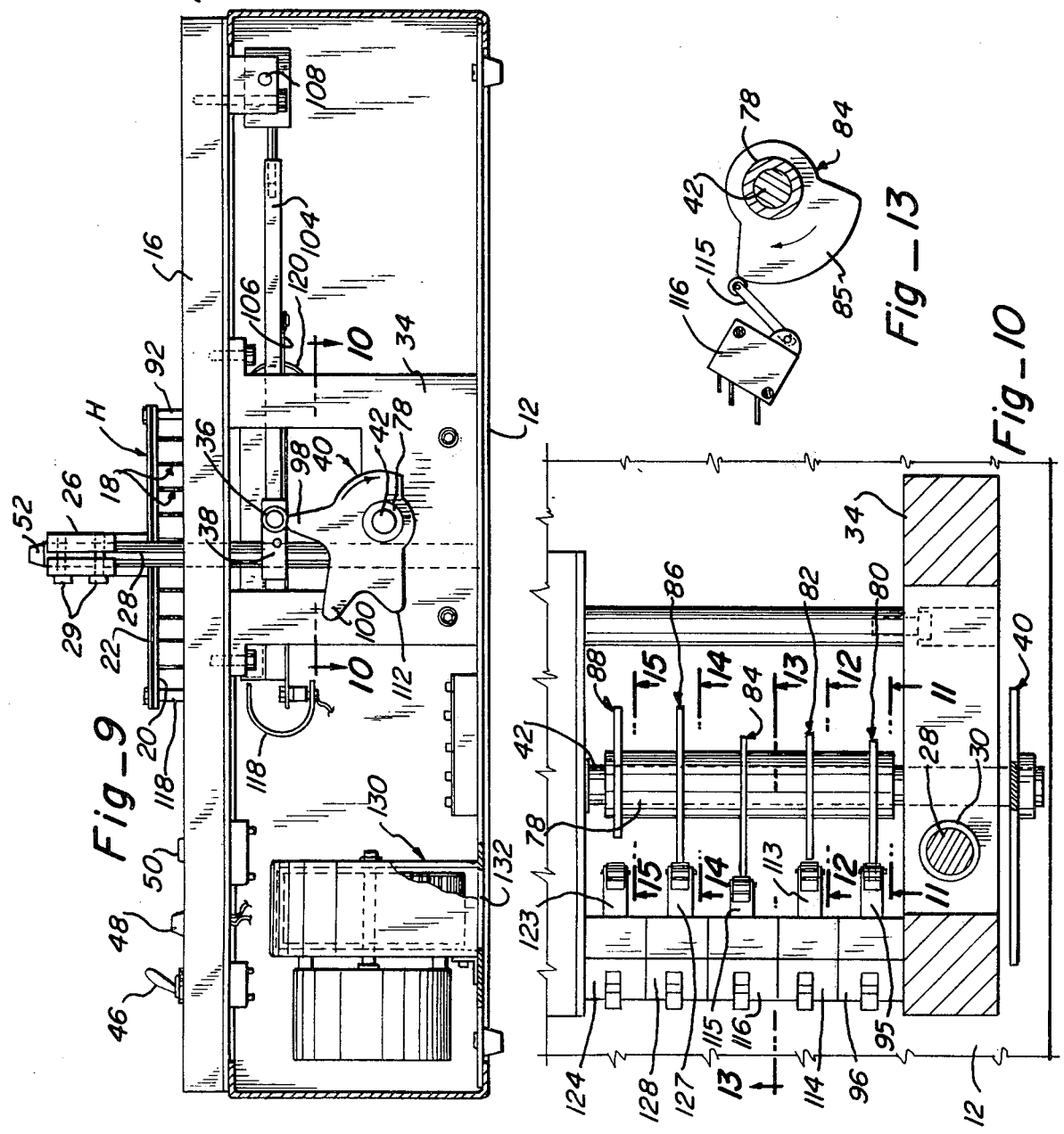

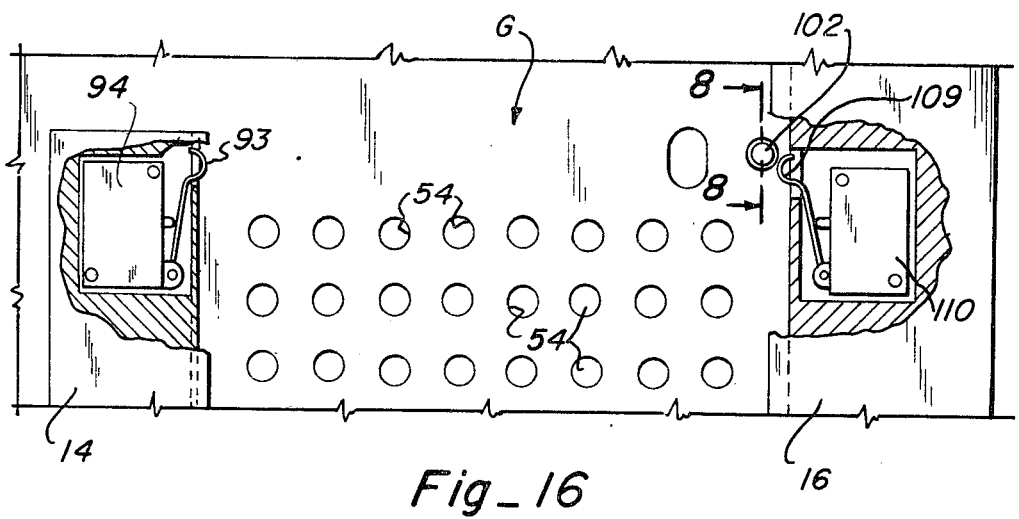
Fig_16
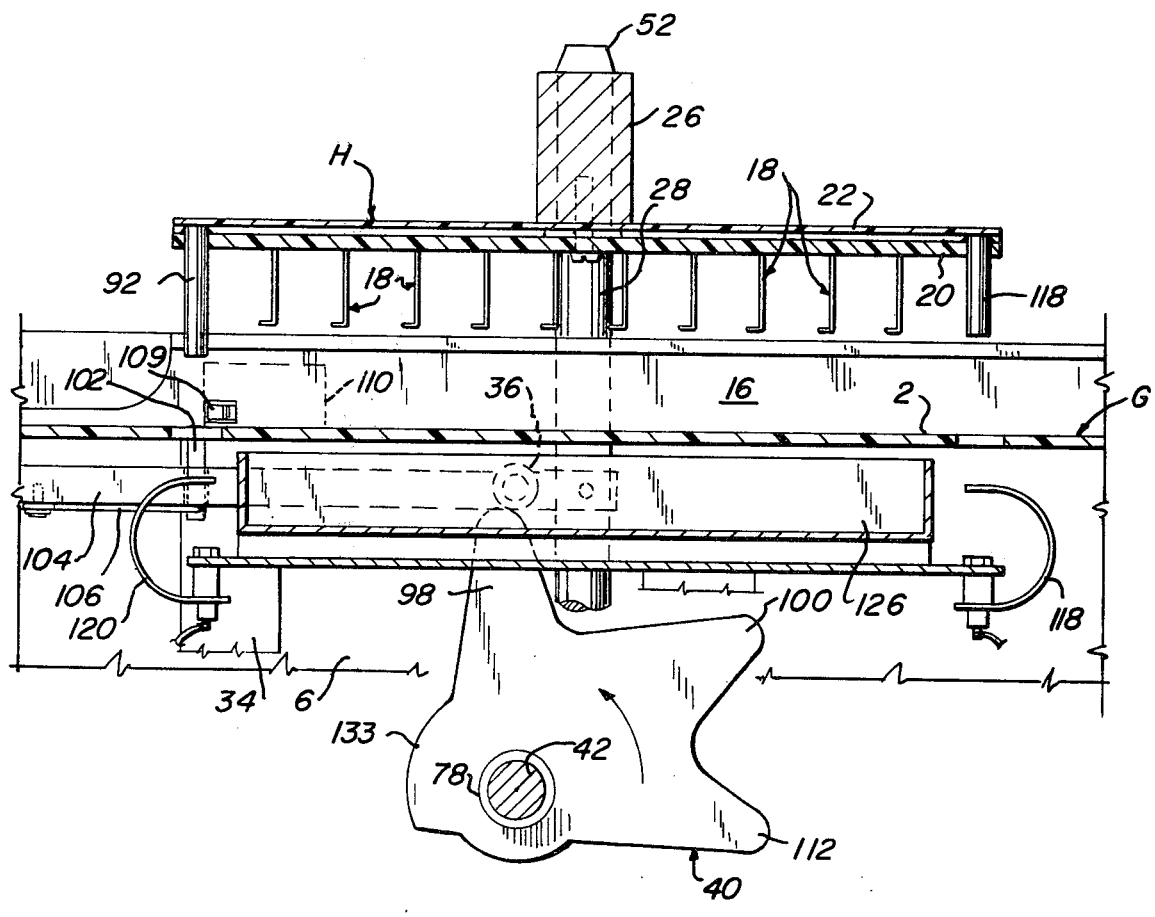
Fig_17

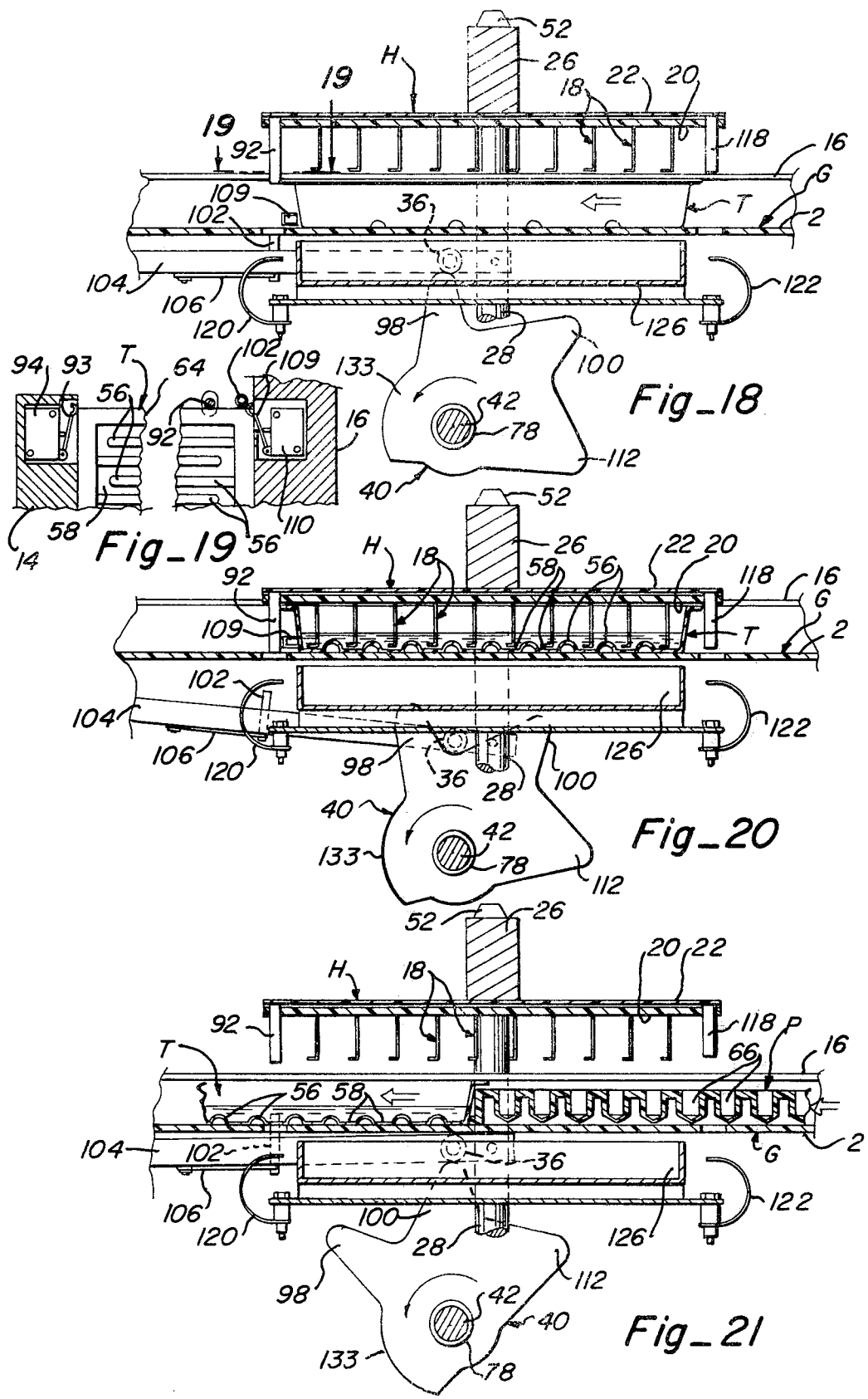

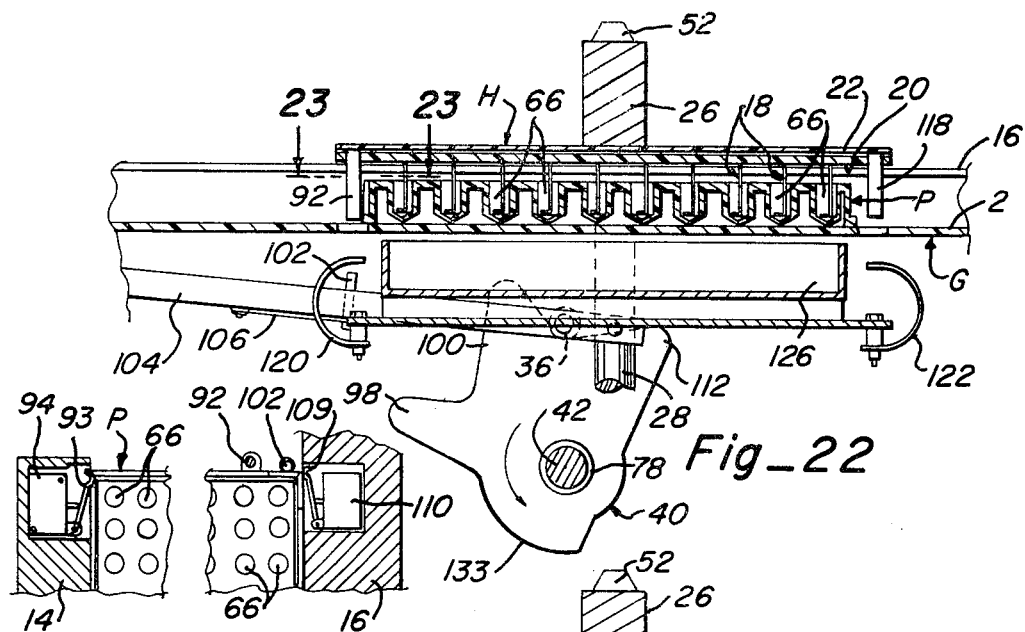
Fig_22
Fig_23
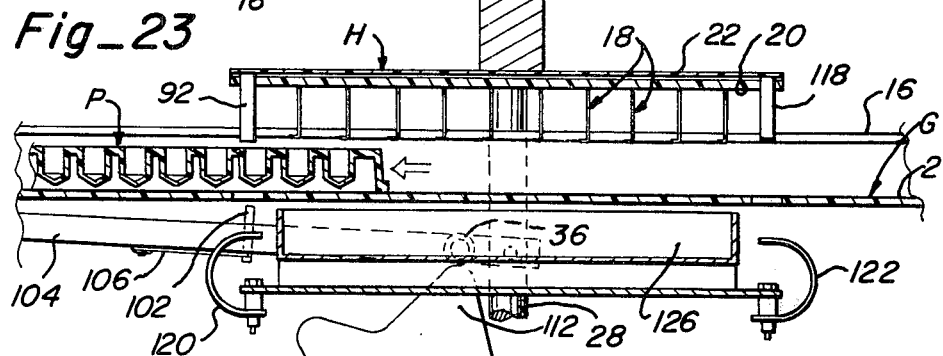
Fig_24
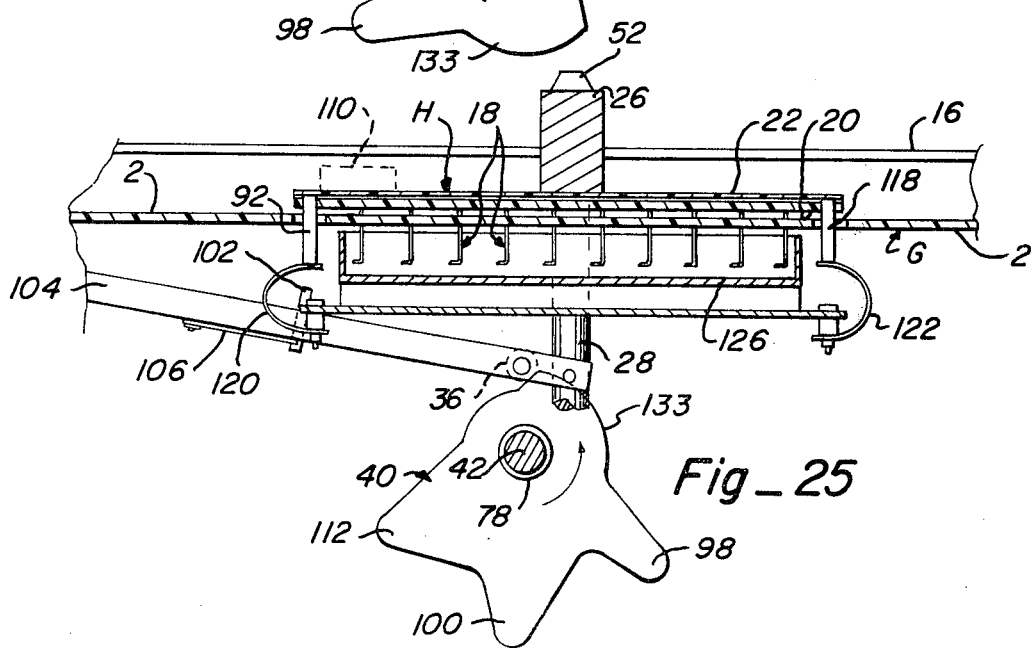
Fig_25

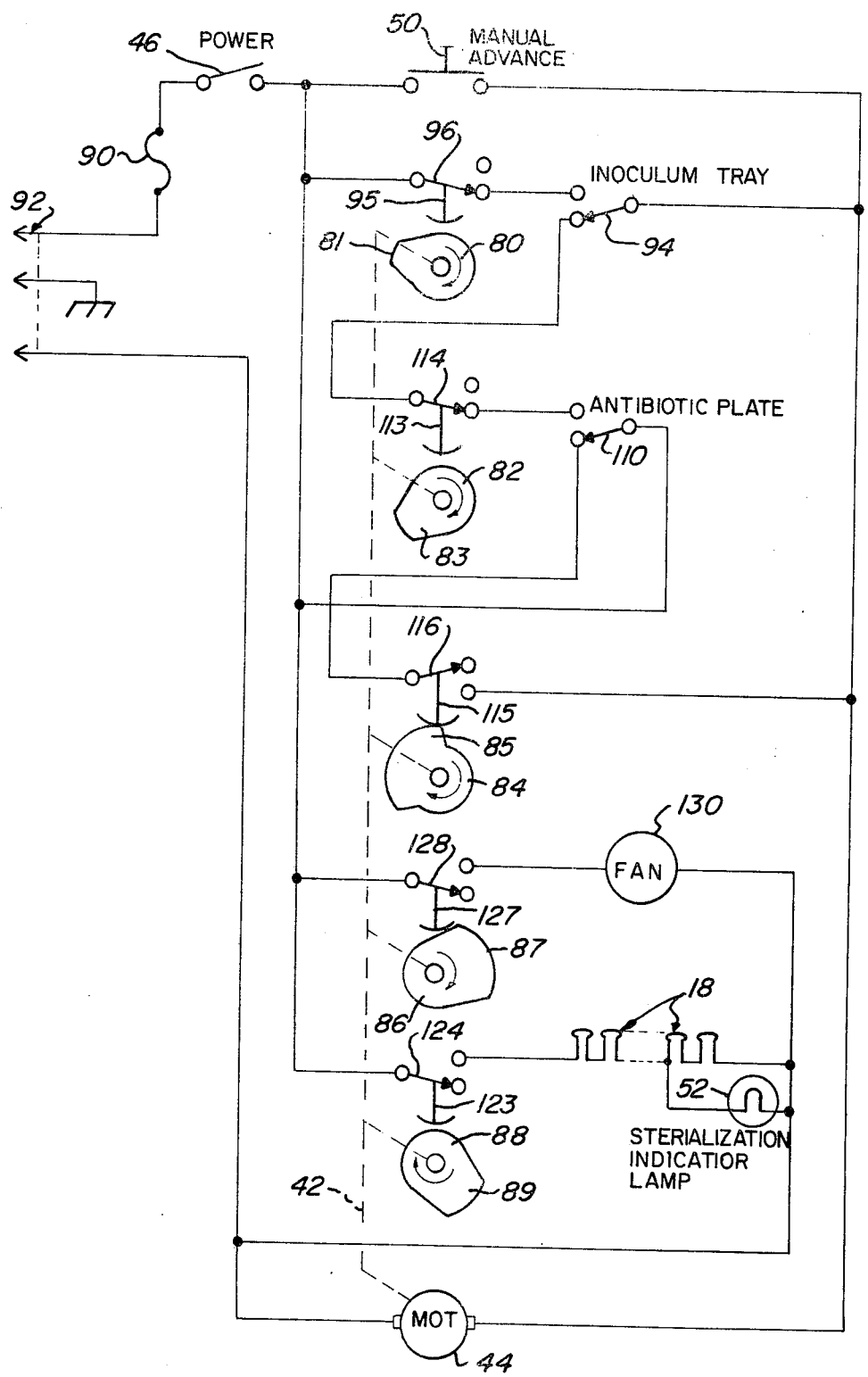
Fig_26

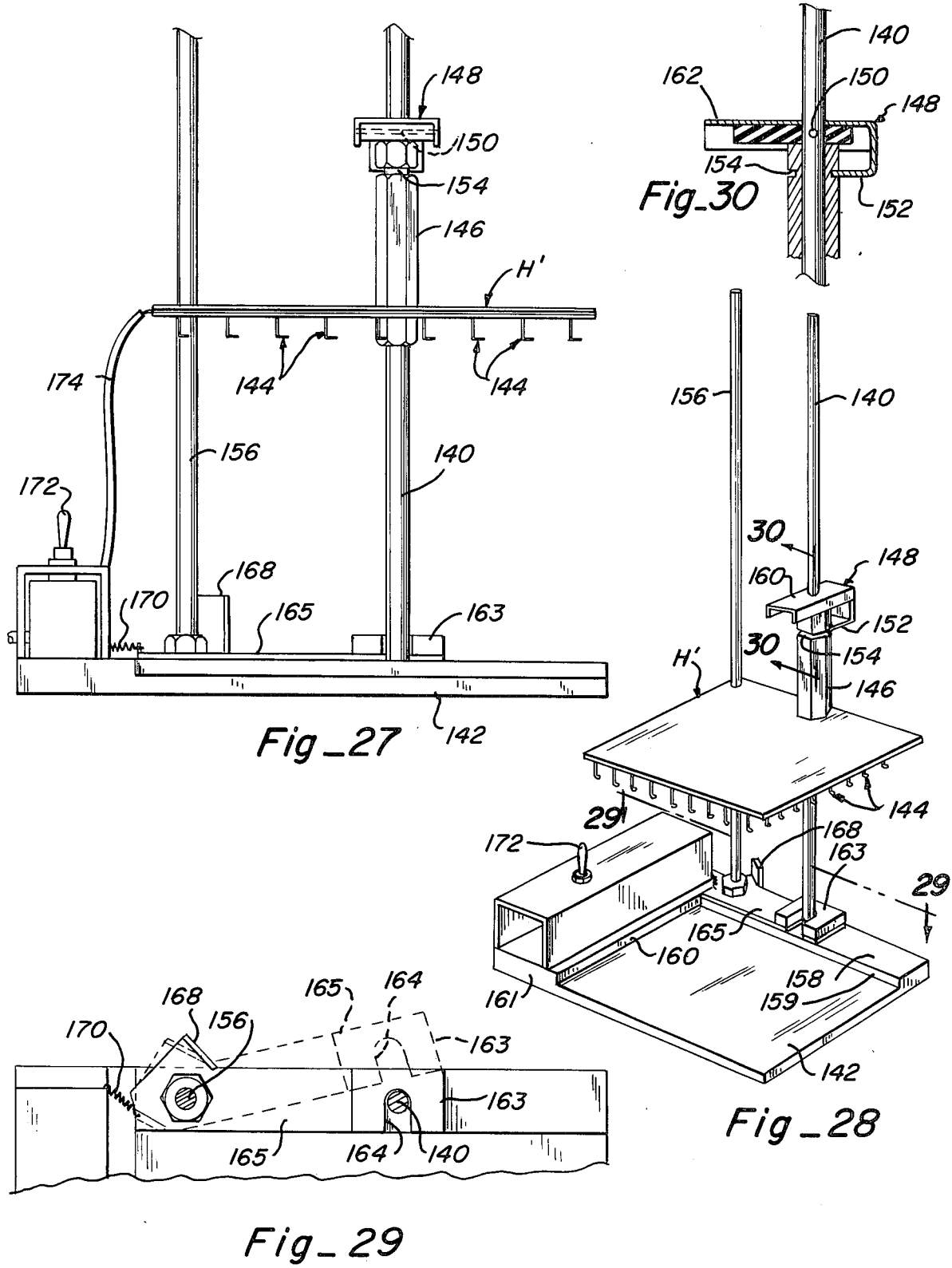

INOCULATOR

BACKGROUND OF THE INVENTION

1. Field of the Invention

Antibiotic plates are sold for use in hospital and medical laboratories wherein the plate includes a plurality of wells, each of which contains different antibiotics at different concentrations and some of the wells may serve as control wells. An inoculum is placed on bacterial loops corresponding in number to the number of wells or microtubes in the plate. The loops are then dipped into the wells so that the inoculum is diluted in the antibiotic. The plates then can be studied to ascertain bacterial growth, if any, in the wells of different concentrations and in the control wells to determine the amount of antimicrobic required to inhibit or kill the bacteria. After the inoculum has been dispersed into the wells, the loops are then sterilized by heating them to a very high temperature whereupon they can be re-used for placing inoculum into the wells of another antibiotic plate.

1. Description of the Prior Art

Various devices, both manual and automatic, have been devised for inoculating an antibiotic or antimicrobic plate in the manner described above. One prior art device includes a head or support mounted for upward and downward manual movement by means of a level arm wherein the supports contains a plurality of downwardly depending loops which are spaced for dipping first into a tray of inoculum and then subsequently into an antibiotic plate so that the inoculum on each of the loops is dispersed into the wells of the plate. After the support has been raised so that the loops are above the plate and the latter has been removed the support is then lowered so that the loops are positioned within an oven which is heated by three tungston halogen quartz bulbs for a period of 20 seconds. The bulbs each have a rating of 500 watts.

One difficulty with this apparatus is that if the antibiotic tray is not perfectly aligned, one or more of the loops may be bent upon the lowering of the support. Furthermore, the heating of the loops by the bulbs relies on convection heating wherein the oven temperature is about 600° F whereas the temperature to which the loops are heated is only about 500° F. As a result, protein becomes baked on the loops each time they are heated and builds up to the point where it must be cleaned off or the loops must be replaced. Furthermore, the energy consumption by the three 500 watt bulbs over the 20 second period is so substantial that the apparatus must be water cooled. Finally, the inoculum trays are constructed in such a manner that it requires at least 25 to 30 milliliters of inoculum to fill the tray sufficiently for dipping the loops therein.

An automatic inoculator is used in the prior art wherein an antibiotic plate is positioned adjacent to an inoculating tray and an oven containing heating coils is located adjacent the antibiotic plate. A head, having a plurality of tubular members with depressions in the end thereof for receiving extremely small amounts of inoculum, on the order of one microliter, is mounted for sequential movement from the inoculating tray to the antibiotic plate and then to the oven. The oven is heated by a pair of heating coils having a rating of 750 watts for a time period of 20 to 30 seconds. In this device, the heating coils run continuously at a temperature of about 600° F and maintain the oven at a temperature of only about 500° F. Thus, the same problem of protein being baked on the loops and building up occurs with this device.

Additional problems which are common to both of these prior art devices is that during the sterilization cycle an odor is given off by the burning inoculum and there may be bacterial contamination of the air which could be harmful to those working in the area. In addition, this odor is unpleasant to people working around the equipment. Finally, each of the devices requires cooling coils around them wherein water is circulated from a tap so that the ovens are kept at a tolerable temperature.

SUMMARY OF THE INVENTION

In accordance with the present invention in one embodiment, an inoculator is provided having means to position an inoculum tray, means responsive to positioning of the tray to dip rows of bacteriological transfer loops at a constant rate of speed in the inoculum raise them again, means to position an antibiotic plate, means responsive to positioning of the antibiotic or antimicrobic microtube plate to dip the loops in the plate at the same constant rate of speed to disperse discrete amounts of inoculum in the wells of the plate means responsive to removing the plate to sterilize the loops at the vaporizable temperature of the inoculum. The inoculum tray includes parallel grooves and ridges in the bottom thereof wherein the grooves correspond in spacing to the position of the rows of bacteriological loops so that a minimum amount of inoculum is required in the tray for the inoculation. Also, the ridges minimize sloshing of the inoculum. Following the sterilizatiion the loops are air cooled by drawing the air past the loops and discharging it to the exterior of the chamber.

More specifically, the invention contemplates a housing above which a head or support for a plurality of bacteriological loops arranged in loops is supported for vertical reciprocation in response to activation of a drive motor. A guideway is disposed on the housing beneath the head when the latter is in raised position for positioning both an inoculum tray and an antibiotic plate for activation of the reciprocal movement of the head. In this regard, the inoculum tray when slid into the guideway and properly positioned will close a switch which energizes the motor to lower the head into the inoculum tray and raise it again thereby placing a discrete amount of inoculum such as 5 microliters on each loop. After the head is returned to raised position, the inoculum tray is pushed out of the guideways by insertion of an antibiotic plate. When the plate is in proper position and the inoculum tray removed, it energizes the motor to lower the head again at a constant speed and place the inoculum samples on each loop into wells in the antibiotic tray by dilution and then return the head to the raised position. The motor means is again energized by removal of the antibiotic plate whereupon the head is lowered to its lower most position whereby the loops are resistance heated to a temperature approaching on the order of 1800° F to 3000° F for three to six seconds to volatize all remaining inoculum remaining on the loops. Thereafter, the slightly off raises off the surface of the housing and the blower is energized to draw the air in past the head blowing away any ash remaining on the loops and drawing all odors and ashes through the blower whereby they may be discharged outside of the chamber. At the conclusion of a 15 second cooling cycle, the head returns to its upper-most position and the blower turns off. The apparatus is now positioned for beginning another cycle.

In another embodiment, a head is allowed to free-fall after the transfer loops are dipped in an inoculum and to disperse the inoculum by percussion into wells of an antibiotic plate upon the head striking a stop member. Thereafter, the transfer loops may be resistively heated to sterilize them.

BRIEF DESCRIPTION OF THE DRAWINGS

FIG. 1 is a perspective view of an inoculator constructed in accordance with the present invention;

FIG. 2 is an enlarged vertical section, taken along line 2—2 of FIG. 1, showing an inoculum tray in position and the location of the timing cams;

FIG. 3 is a perspective view of an inoculum tray constructed in accordance with this invention;

FIG. 4 is an enlarged horizontal section, taken along line 4—4 of FIG. 3, showing the construction of the bottom of the inoculum tray;

FIG. 5 is a top plane view of the antibiotic plate as used with this invention;

FIG. 6 is an enlarged horizontal section, taken along line 6—6 of FIG. 5, showing details of the microtubes or wells in the antibiotic plate;

FIG. 6a is an enlarged section, taken along line 6a—6a of FIG. 5 showing the corner construction of the plate in FIG. 5;

FIG. 7 is an enlarged fragmentary perspective view showing the bacteriological loops and the electrical connections therefor;

FIG. 8 is an enlarged fragmentary horizontal section, taken along line 8—8 of FIG. 16, showing a stop pin and switch for the inoculum tray;

FIG. 9 is a horizontal section taken from the rear of the inoculator, along line 9—9 of FIG. 1, showing the lift cam and the blower construction;

FIG. 10 is an enlarged fragmentary horizontal section, taken along line 10—10 of FIG. 9, showing the cam and switch locations;

FIG. 11 is an enlarged horizontal section, taken along line 11—11 of FIG. 10, showing the position of the inoculum tray cam at the beginning of a cycle;

FIG. 12 is an enlarged horizontal section, taken along line 12—12 of FIG. 10, showing the position of the antibiotic plate cam at the beginning of a cycle;

FIG. 13 is an enlarged horizontal section, taken along line 13—13 of FIG. 10, showing the position of the head lowering cam at the beginning of a cycle;

FIG. 14 is an enlarged horizontal section, taken along line 14—14 of FIG. 10, showing the position of a fan operating cam at the beginning of a cycle;

FIG. 15 is an enlarged horizontal section, taken along line 15—15 of FIG. 10, showing the position of a heater operating cam at the beginning of a cycle;

FIG. 16 is an enlarged horizontal section through the guideways of the inoculator, taken along line 16—16 of the FIG. 1, with parts broken away to show details of the switches for the inoculum tray and the antibiotic plate;

FIG. 17 is an offset vertical section, taken along line 17—17 of FIG. 2, showing the position of the head at the beginning of a cycle and showing further details of the stop pin construction;

FIG. 18 is a vertical section, similar to FIG. 17, but on a reduced scale, showing an inoculum tray being inserted in the guideways;

FIG. 19 is an enlarged fragmentary horizontal section, taken along line 19—19 of FIG. 18, showing the inoculum tray positioned against the stop and closing a switch for activation of the inoculator;

FIG. 20 is a vertical section, similar to FIG. 18, but showing the head lowered so that the bacteriological loops extend into the inoculum within the inoculum tray;

FIG. 21 is a vertical section, similar to FIGS. 18 and 20, but showing the head raised wth inoculum in the loops and showing an antibiotic plate pushing an inoculum tray through the guideways;

FIG. 22 is a vertical section, similar to FIGS. 18, 20 and 21, but showing the head lowered so that the loops are in the wells of the antibiotic plate for dispersing the inoculum on the loops into the wells;

FIG. 23 is a fragmentary enlarged horizontal section, similar to FIG. 19, but showing an antibiotic plate in position in the guideways against the stop means and activating the appropriate switch;

FIG. 24 is a vertical section, similar to FIGS. 18, 20, 21 and 22, but showing the head raised after dispersion of an inoculum in the antibiotic plate and the antibiotic plate being removed;

FIG. 25 is a vertical section, similar to FIGS. 18, 20, 21, 22 and 24, but showing the head just after it is raised from its lowermost position during the heating or sterilization cycle toward the cooling cycle position;

FIG. 26 is a circuit diagram showing the position of the cams of FIGS. 11-15 at the beginning of a cycle;

FIG. 27 is a side elevation of an alternative embodiment of this invention wherein inoculum is dispensed from the loops into the antibiotic plate by percussion;

FIG. 28 is a perspective view of the inoculator of FIG. 27.

FIG. 29 is an enlarged horizontal section, taken along line 29—29 of FIG. 28 showing the latch of FIG. 28 in open position in dotted lines; and FIG. 30 is an enlarged vertical section, taken along line 30—30 of FIG. 28, showing details of the latch mechanism for the head.

DESCRIPTION OF THE PREFERRED EMBODIMENTS

In accordance with this invention, an inoculator is provided which has a frame or housing F comprising a top surface 2 supported by front and rear walls 4 and 6, respectively, and by end walls 8 and 10, all as best seen in FIGS. 1 and 2. The frame F also includes a bottom 12 to complete the enclosure. Conveniently, the top surface may be made of some durable countertop-type material such as "Formica". At the center of top surface 2, a guideway G is formed by means of a outer guide rail 14 and an inner guide rail 16 through which an inoculum tray T and an antibiotic plate P may be moved in a manner and for a purpose to be described. Mounted over guideway G for vertical reciprocal movement is a head H from which depend a plurality of rows of bacteriological transfer loops 18.

Head H comprises a lower plate 20 to which transfer loops are attached, in a manner to be described, and an upper plate 22 to which the lower plate is attached as by means of screws 24 extending through upper plate 22 into support arm 26, as best seen in FIG. 2. Support arm 26 is clamped to the upper end of reciprocating post 28 by means of set screws 29. Post 28 is slidably received in an upper sleeve 30 mounted in inner rail 16 and a lower sleeve 32 in a support 34 attached to bottom 12, as shown in FIG. 2. A cam follower 36 is held on a shaft by retainer 37 on bracket 38. Bracket 38 is fixedly attached to post 28 and will cause post 28, and hence Head H, to raise and lower in response to movement of positioning cam 40, as described below. Positioning cam 40 is rotatably driven through cam shaft 42 by means of motor 44.

Also mounted on frame F is an on-off switch 46 and indicator light 48 and a manual advance button 50, for a purpose to be described. Also, there is an indicator light 52 mounted on top of support arm 26 which is illuminated during the sterilization cycle. As will be more fully explained below, during the sterilization cycle the head is moved to its lowermost position in which transfer loops 18 extend through openings 54 on top surface 2 within guideway G, as best seen in FIGS. 2 and 16.

In accordance with this invention, a novel inoculum tray T is provided which is best seen in FIGS. 3 and 4. It is necessary to fill the trays to a depth of two to three millimeters with inoculum in order to have sufficient depth for dipping of the transfer loops. This inoculum is a bacterial suspension in broth; the bacteria may originate from blood, urine, sputum or the like. In a conventional tray, about 30-40 millileters of inoculum is required to fill the tray to required depth. The tray of this invention includes a novel bottom having a plurality of spaced parallel ridges 56 forming spaced parallel gr therebetween. Conveniently, as best seen in FIG. 3, every other ridge 56 starts adjacent side wall 60 and terminates just short of side wall 62. Similarly, the other alternate pairs of ridges 56 start adjacent side wall 62 and stop just short of side wall 60. This causes grooves 58 to form a somewhat serpentine path back and forth across the bottom of the tray and conveniently, the grooves are spaced so that the rows of transfer loops are aligned with the grooves for picking up the liquid therein. Obviously, since the ridges occupy a great deal of the surface area of the bottom of tray T, a substantially lesser amount of inoculum is needed, such as about 12.5 millileters. This reduced amount will still bring the depth of the liquid to two to three millimeters within the grooves which is sufficient for the transfer loops. Also, the ridges prevent sloshing of inoculum in the tray when it is handled. The upper edge of the tray terminates in a peripheral lip 64 which serves to close a switch to activate the dipping cycle of the inoculator when the tray is properly positioned in the guideway G, as will be described.

The antibiotic or antimicrobic plate P, shown in FIG. 5, is generally similar in construction to conventional plates in that it is provided with a plurality of wells or microtubes 66 and can conveniently have eight rows of ten microtubes or wells each. Typically, nine rows of the tray will be provided with nine different antibiotics at eight different concentrations. Each well will contain about 99 microliters of a broth which serves as a nutrition for bacteria which grow and reproduce and about one microliter of the antibiotic. The last row serves as a control wherein some wells contain broth to which bacteria are added during inoculation and some remaining wells do not receive any inoculum because there are no transfer loops corresponding to these wells. In other words, the head H has 76 transfer loops whereas the plate contains 80 wells, but the number of loops is variable.

The particular antibiotic plate shown in FIGS. 5 and 6 is manufactured by Pasco Laboratories of Wheatridge, Colorado and is particularly designed for use with the inoculator of this invention. In this regard, plate P includes a thin peripheral lip 68 that extends around substantially the entire periphery of the plate except for one corner which has a raised lip 70 as seen in FIG. 6a, which serves to orient the plate properly in guideway G of the inoculator and also serves to activate a switch as will be described later to initiate the inoculation cycle.

The transfer loops 18, as shown in FIG. 7, are connected in series and include a loop 72 formed at the lower extremities of parallel leg wires 74 which are soldered at their upper ends to connecting wires 76 mounted on the upper side of upper plate 22, as seen in FIG. 7. Conveniently, the loop 72 and leg wire 74 are made of a high strength platinum alloy which will permit them to be heated to a very high temperature, such as 3000° F, during the sterilization cycle.

At the beginning of a cycle, positioning cam 40 is in the position shown in FIGS. 9 and 17. Cam shaft 42 has a plurality of logic cams mounted on a sleeve 78, as best seen in FIGS. 2 and 10. These cams are shown in their initial position in FIGS. 11-15 and FIG. 26. The first three cams, i.e., cams 80, 82 and 84, respectively, initiate the logic of the inoculator as will be described while the other two cams, i.e., 86 and 88 serve to initiate certain mechanical operations of the inoculator, also to be described.

To initiate operation of the inoculator, power switch 46 is closed, this switch being connected through fuse 90 to a grounded outlet 92, as shown in FIG. 26. This will cause indicator light 48 to be illuminated to show that the inoculator has been turned on. A tray T which has been previously filled with enough inoculum 90 to fill grooves 58 is inserted as shown in FIGS. 1 and 2, between rails 14 and 16 until an end wall of the tray abuts against stop pin 92, which depends from head H to a point below loops 18 as seen in FIGS. 18 and 19. The positioning of tray T against stop 92 causes the peripheral lip 64 to engage arm 93 of switch 94 to close the switch. This completes the circuit to motor 44 through normally closed switch 96, as seen in FIG. 26.

At the beginning of the cycle, cam follower 36 is at the top of cam lobe 98, as shown in FIGS. 9, 17 and 18. Thus, upon activation of motor 44 positioning cam 40 will begin to rotate in the direction shown by the arrows so that head H is moved downwardly under the influence of gravity. Cam follower 36 will ride along the edge of lobe 98 until it reaches the position shown in FIG. 20 wherein loops 18 are now dipped in the inoculum as shown in FIG. 20 and pick up about 5 microliters of inoculum. It can be seen from FIG. 20 that the loops are disposed in the groove 58 between ridges 56 of the tray T.

As cam 40 continues to turn, cam follower 36 will begin to ride up on a second cam lobe 100 until it reaches the tip thereof as shown in FIG. 21. It will be noted that cam lobe 100 is longer than cam lobe 98 and therefore the head H is raised to a higher position than before wherein pin 92 now clears the top of Tray T so that the tray may be pushed on through the guideways by the insertion of an antibiotic plate P, as seen in FIG. 21.

The plate P will move through guide rail G until it engages stop pin 102 which projects through an opening in top surface 2, as shown in FIGS. 21 and 23. The pin is connected to an arm 104 by means of a leaf spring 106 and moves up and down in response to movement of arm 104 which is pivotally connected at one end to post 28 and pivoted at the other end in a bracket 108 connected to the frame F, as shown in FIG. 9. The stop pin 102 is resiliently mounted so that should there be any misalignment when the arm 104 moves upwardly, the pin would be depressed by the tray or any object that it should strike as it comes through top surface 2.

When antibiotic plate P moves against stop 102, as shown in FIG. 23, raised lip 70 will depress arm 109 of switch 110 thereby completing the circuit to motor 44 to initiate the inoculation cycle, as shown in FIG. 26, causing the cam shaft 42 and all of the associated cams to begin rotating again. During this inoculation cycle, positioning cam 40 will rotate from the position shown in FIG. 21 through the position shown in FIG. 22 and finally to the position shown in FIG. 24. As can be seen, cam follower 36 will ride along the edge of the positioning cam to cause the head H to be lowered at a constant speed so that transfer loops 18 are lowered into wells 66 of antibiotic plate P and submerged in the broth in the respective wells so that the inoculum on the loops is dispersed in the broth.

As cam follower 36 rises up on lobe 112 of positioning cam 40, head H is raised after dispersing the inoculum in the transfer loops 18 and as it reaches the tip of lobe 112, lobe 83 of logic cam 82 hits arm 113 of switch 114 whereupon the normally closed switch is moved from the position shown in FIG. 26 to the open position. This will result in the de-energization of motor 44 and will again stop the rotation of cam shaft 42. Since lobe 112 is lower than lobe 110, pin 102 on arm 104 will now be below the bottom of top surface 2 so that antibiotic plate P may be pushed out the guideway, as shown in FIG. 24. When plate P is removed, switch 110 then returns to the position shown in FIG. 26 and since lobe 85 of cam 84 has now moved past the arm 115 of switch 116 the switch moves to its normally closed position which, as can be seen in FIG. 26, will again complete the circuit to motor 44 and begin rotation of cam shaft 42.

During this sterilization cycle, the head will move from the raised position of FIG. 24 to the lowered position whereby pin 92 on the head as well as a corresponding pin 118 thereon engage electrical spring contacts 120 and 122, respectively, as shown in FIG. 25. Pins 92 and 118 are electrically connected to loops 18 by connecting wires 76 of FIG. 7. Thus, with the head in the lowered position head H engages top 2, a circuit to the transfer loops 18 is completed since lobe 89 of cam 88 now engages arm 123 of switch 124, as shown in FIG. 26, whereby the loops are resistively heated to a temperature approaching 3000° F to completely volatilize any inoculum or antibiotic on the loops. Any spattering which occurs during sterilization will be contained within tray 126 located below the guideways, as shown in FIG. 25 and since head H is in engagement with top surface 2 no inoculum can spatter up into the guideways. Conveniently, lamp 52 which is mounted in support arm 26 of head H is connected in parallel with at least one of the transfer loops 18 as shown in FIG. 26 and therefore becomes illuminated during the heating cycle to indicate that the sterilization operation is underway. Advantageously, the sterilization cycle only lasts for five seconds thereby keeping the power consumption at a relatively low level.

As lobe 89 of cam 88 rides off of arm 123 the circuit to transfer loops 18 is broken by the opening of switch 124, whereupon positioning cams 40 will have rotated to the position whereby a low but relatively long lobe 133 will engage cam follower 36 and begin to raise head H off of top surface 2 a short distance, as shown in FIG. 25. At this point, lobe 87 of cam 86 engages arm 127 of switch 128 thereby closing the circuit to fan 130 of FIG. 26 so that the fan draws air in around the head thereby cooling transfer loops 18 which have now been de-energized due to the opening of switch 124. As best seen in FIG. 9, fan 130 is vented through an opening 132 in bottom 12. Conveniently, this opening may be connected by suitable tubing (not shown) to vent the noxious odors and vapors outside of the room. This arrangement virtually eliminates any odor around the inoculator. The cooling cycle continues until lobe 85 of cam 84 rides off of arm 115 thereby breaking the circuit to motor 44. Also, at this point the circuit to fan 130 will be broken and the positioning cam will again be back to the starting position shown in FIG. 18. Now the inoculator is ready for the insertion of a new tray of incoulum to begin a new cycle.

Manual switch 50 permits the energization of motor 44 so that all of the cycles can run without the positioning of inoculum tray T or antibiotic plate P. This may be necessary should a malfunction occur or during normal servicing of the inoculator.

An alternative and less complex inoculator is shown in FIGS. 27-30 wherein a head H' is support for reciprocal movement along a post 140 mounted on a base 142. The head is provided with a plurality of transfer loops 144 which depend from the head and are arranged in rows, as in the previous embodiment. The head is mounted on a slide member 146 projecting upwardly from the head which can be releasably connected to a latch 148 which is pivoted on post 140 by means of a pivot pin 150 shown in FIG. 30. The latch has a depending angular arm 152 which engages a peripheral groove 154 in member 146 to hold head H' in a raised position.

Conveniently a guide rod 156 is mounted on a raised portion 158 of base 142 and extends parallel to rod 140 and through head H' so that the head will not twist or turn as it moves from its raised position in which it is locked by latch 142 and a lowered position. In operation, a tray of inoculum is placed on base 142 and positioned by the edge 159 of raised portion 158 and edge 160 of raised portion 161 which acts as a guideways to align the tray. The head H' is manually lowered into the inoculum to pick up the inoculum on the respective loops 144. The head is then raised and locked by latch 148 in groove 154 to hold the head in a raised position. The tray of inoculum is then removed and replaced by an antibiotic plate which is also made to rest on base 12 and is aligned by perpendicular edges 159 and 160. Lever 162 of latch 148 is depressed to release arm 152 from groove 154 whereby head H' falls freely until it strikes stop member 163 which will stop the head H' so that loops 144 are just above the top of the antibiotic plate. The percussive force of the head H' hitting stop 163 will cause the inoculum on the loops 144 to be shaken off into the wells of the plate.

As best seen in FIGS. 28 and 29, the stop 163 includes a recess 164 which stradles post 140 and is pivoted by means of an arm 165 about guide rod 156 and can be pivoted from the solid line position in FIG. 29 wherein it is engageable by head H' to an open position by means of lever 168. This lever can be engaged by the finger or thumb of the operator to pivot arm 165 and raised stop 163 in a counterclockwise direction, as viewed in FIG. 29, against the force of spring 170 as when head H' is lowered into the inoculum tray to place inoculum on transfer loops 144.

After the inoculum is dispersed into the antibiotic plate, head H' can be raised so that it is again engaged by latch 148 and held in raised position. Then the antibiotic plate can be removed from base 142. By throwing switch 172, current can be supplied by wire 174 to transfer loops 144 to heat them to a sufficient temperature to sterilize them and volatilize any inoculum or antibiotic material thereon. As soon as the sterilization procedure has been accomplished, switch 172 can be opened and then the cycle is ready to begin again. Of course, the operator should wait a few moments for the transfer loops 144 to cool.

From the foregoing, the advantages of this invention are readily apparent. In one embodiment, an inoculator has been provided which operates on a timing cycle in response to the positioning of the inoculum tray and the antibiotic plate. Because of the novel arrangement in which the inoculum tray and the antibiotic plate are received in guideways, the operation is sequentially accomplished in a timely manner by operator-initiated action which results in a faster cycling time than was possible in prior art devices. This invention utilizes less energy per cycle and higher heating temperatures for the sterilization portion of the cycle.

Discrete amounts of inoculum may be placed in the antibiotic plate wells either by dispersions as in one embodiment or by percussion as in another embodiment. This results in repeatable and valid test results.

The invention has been described in detail with particular reference to preferred embodiments thereof, but it will be understood that variations and modifications can be effected within the spirit and scope of the invention.

What is claimed is:

1. An inoculator for placing discrete amounts of inoculum into each of a plurality of wells in an antibiotic plate, said inoculator comprising:
   a support for alternatively holding a tray containing a quantity of inoculum therein and an antibiotic plate having wells therein, wherein each well contains broth and/or antibiotics, said support having a plurality of spaced openings therein;
   means for positioning either the inoculum tray or the antibiotic plate on said support;
   a head mounted above said support for reciprocal movement toward and away from said support;
   a plurality of transfer loops depending from one side of said head and aligned with said opening in said support for being dipped selectively in the inoculum tray and in the respective wells of the antibiotic plate when said head is moved toward said support; to cause inoculum on said transfer loops to be placed in the wells of the antibiotic plate in discrete amounts.
   means for causing said head to reciprocally move from a first position spaced from said support to a second position wherein said transfer loops are selectively dipped in the inoculum tray and in the respective wells of the antibiotic plate and a third position wherein said transfer loops extend through said spaced openings in said support for sterilization of said transfer loops; and
   means for causing inoculum on said transfer loops to be placed in the wells of the antibiotic plate in discrete amounts; and tray means located below said support in which said rows of transfer loops are simultaneously sterilized by resistance heating while said head is in said third position with said transfer loops extending through said openings in said support.

2. An inoculator for placing discrete amounts of inoculum into each of a plurality of wells in an antibiotic plate, said inoculator comprising:
   a support for alternatively holding a tray containing a quantity of inoculum therein and an antibiotic plate having wells therein, wherein each well contains broth and/or antibiotics;
   means for positioning either the inoculum tray or the antibiotic plate on said support;
   a head mounted above said support for reciprocal movement toward and away from said support;
   a plurality of transfer loops arranged in rows and depending from one side of said head for being dipped selectively in the inoculum tray and in the respective wells of the antibiotic plate when said head is moved toward said support causing inoculum on said transfer loops to be placed in the wells of the antibiotic plate in discrete amounts;
   means for causing said head to move toward or away from said support;
   means for sterilizing said transfer loops by resistance heating;
   drive means for reciprocally moving said head toward and away from said support;
   first switch means closed by placing the inoculum tray in said positioning means to energize said drive means to cause said head to be lowered toward said support to dip said transfer loops in the inoculum tray and raised said head above said support so that said loops are positioned above said inoculum tray with inoculum in each of said loops;
   second switch means closed by placing the antibiotic plate on the support means in alignment by said positioning means to energize said drive means to dip said loops in the wells of the antibiotic plate to disperse the inoculum thereon into the wells and to raise the head above said support so that the loops are spaced above the plate;
   third switch means responsive to de-energize said drive means when said head is in raised position, said second switch means responsive to removal of said antibiotic plate to re-energize said drive means to lower said head until the head engages the surface of said support;
   means responsive to the lowering of said head against said support for resistively heating said transfer loops for a predetermined time period to sterilize them; and
   means responsive to partial raising of said head by said drive means for energizing the fan for drawing air between said head and said support surface and past said transfer loops for cooling the same and responsive to further raising of the head for de-energizing said drive means and said fan.

3. An inoculator for placing discrete amounts of inoculum into each of a plurality of wells in an antibiotic plate, said inoculator comprising:
   a support for alternatively holding a tray containing a quantity of inoculum therein and an antibiotic plate having wells therein, wherein each well contains a broth and antibiotics;

spaced guideways on said support to facilitate sliding movement of the inoculum tray and antibiotic plate to a preselected position on said support;

a head mounted above said support for reciprocal movement toward and away from said support;

a plurality of transfer loops arranged in rows and depending from said head toward said support;

drive means for raising and lowering said head in timed sequence in response to the positioning of the inoculum tray and antibiotic plate;

a first switch mounted in one of said guideways responsive to the positioning of an inoculum tray for energizing said drive means to lower said head so that said transfer loops are dipped in said inoculum tray and for raising said head above said support so that said loops are positioned above said inoculum tray with inoculum in each of said loops;

second switch means mounted in one of said guideways responsive to positioning the antibiotic plate in said guideways for re-energizing said drive means to move said head toward said support so that transfer loops carrying inoculum are dipped in the wells of the plate and to raise the head above said support so that the loops are spaced above the plate;

means responsive to removal of the antibiotic plate from the guideways for re-energizing said drive means to lower said head to a position against the support surface;

means for resistively heating said transfer loops for a predetermined time to sterilize said transfer loops when said head is lowered against said plate;

exhaust fans means; and means for energizing said exhaust fan means upon partial raising of said head from said support by said drive means for drawing air past said support and said head to cool said transfer loops.

4. An inoculator, as claimed in claim 3, wherein said drive means includes:
a drive motor;
a drive shaft driven by said drive motor at a constant speed;
a positioning cam fixedly attached to said shaft for rotation therewith and having a plurality of lobes thereon; and engageable with the lobes of said cam for moving said head up and down in response of the rotation of said cam.

5. An inoculator, as claimed in claim 4, further including:
a first logic cam fixedly mounted on said drive shaft for rotation therewith for interrupting said circuit to said drive motor when said inoculum tray is positioned on said guideways after said transfer loops have been dipped in said inoculum tray;
a second logic cam fixedly mounted on said drive shaft for de-energizing said drive motor when said antibiotic plate is positioned on said support after said transfer loops have dispersed inoculum in the wells of the antibiotic plate;
a third logic cam means fixedly attached to said drive shaft for energizing said drive motor when said antibiotic plate is removed from said guideways;
a heater cam fixedly mounted on said drive shaft for activating the resistive heating of said transfer loops during a sterilization cycle upon movement of said head against said support; and
a fan cam fixedly mounted on said drive shaft for energizing said fan after completion of said heating cycle of said transfer loops to cool said transfer loops.

6. An inoculator, as claimed in claim 3, wherein said tray includes:
a bottom having a plurality of spaced parallel grooves separated by ridges, the spacing of said grooves corresponding to the rows of said transfer loops and being aligned therewith when said tray is in position on said support means.

7. A tray, as claimed in claim 6, wherein:
said grooves are interconnected at opposite ends thereof to form a serpentine path.

8. An inoculator, as claimed in claim 3, wherein:
said first and second switches are mounted in opposite guideways.

9. An inoculator, as claimed in claim 3, wherein:
said first switch is spaced from said support; and
said second switch is adjacent said support.

* * * * *